United States Patent [19]

Bobechko

[11] 4,433,676
[45] Feb. 28, 1984

[54] SELF-ADJUSTING SPINAL SCOLIOSIS FUSION HOOK

[76] Inventor: Kevin A. Bobechko, 178 St. George St., Toronto, Ontario, Canada, M5R 2N2

[21] Appl. No.: 362,757

[22] Filed: Mar. 29, 1982

[30] Foreign Application Priority Data

Apr. 6, 1981 [CA] Canada .................................. 374769

[51] Int. Cl.³ ............................................... A61F 5/00
[52] U.S. Cl. .................................. 128/69; 128/92 BC; 128/71
[58] Field of Search .................. 128/69, 71, 75, 78, 128/84 R, 84 B, 84 C, 92 R, 92 E, 92 B, 92 BC, 92 RA; 403/326, DIG. 7; 24/230.5 R, 230.5 AD

[56] References Cited

U.S. PATENT DOCUMENTS 3,596,656 8/1971 Kaute .............................. 128/92 D
4,274,401 6/1981 Miskew .............................. 128/69

FOREIGN PATENT DOCUMENTS 286136 of 1971 U.S.S.R. .............................. 128/69

Primary Examiner—C. Fred Rosenbaum
Assistant Examiner—Sherri E. Vinyard
Attorney, Agent, or Firm—Riches, McKenzie & Herbert

[57] ABSTRACT

This invention relates to a medical device, namely a novel clip to be used in conjunction with a Harrington rod for the treatment of spinal disorders. The hook has a body portion with a housing at one end thereof, with a hooked portion at the opposite end. A sleeve is inserted through and is retained in a channel which extends through the housing by a retaining means. Using this clip, it is possible to spread the load over more than one lamina as more than one hook may be used in the procedure. This thus allows a patient to be mobile without external support immediately following surgery which has been impossible with the prior art devices.

14 Claims, 7 Drawing Figures

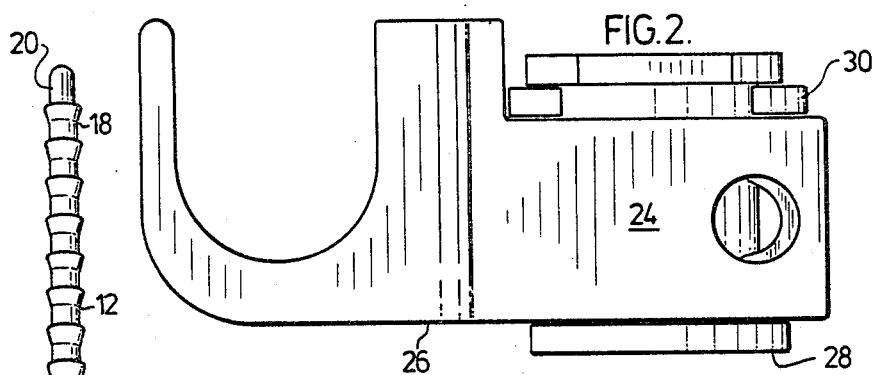
FIG.2.
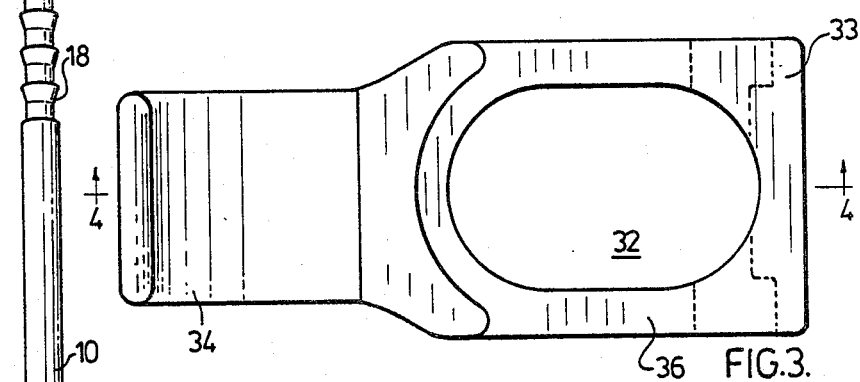
FIG.3.
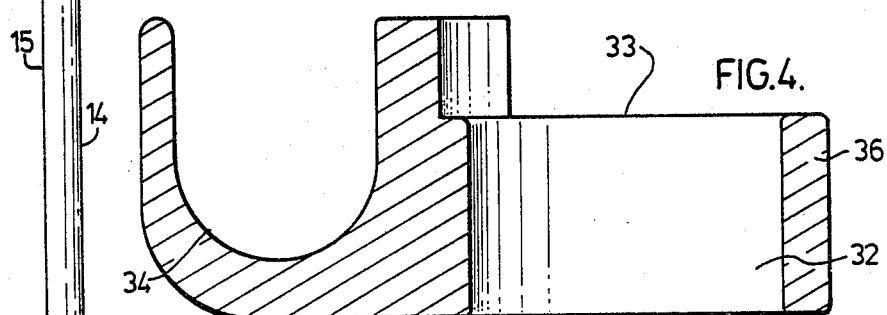
FIG.4.
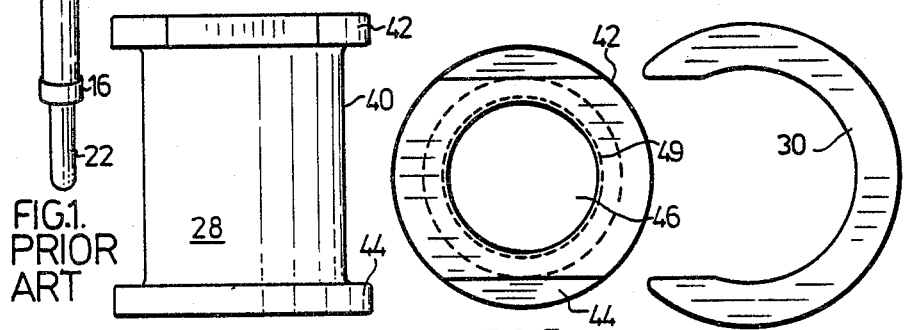
FIG.1. PRIOR ART
FIG.6.   FIG.5.   FIG.7.

SELF-ADJUSTING SPINAL SCOLIOSIS FUSION HOOK

BACKGROUND OF THE INVENTION

1. Field of the Invention

This invention relates to a medical device, and more particularly, to a novel clip to be used in the treatment of scoliosis.

2. Description of the Prior Art

Scoliosis is an abnormal lateral curvature of the spine which affects both young children as well as adults. There are many different types of scoliosis, but the common type seen is on a hereditary basis and is divided into very early mobile flexible curves without structural bony change and those which have fixed organic deformities of a structural nature within the vertebral bodies and adjacent soft tissue and bone structures.

The treatment of scoliosis is dependant on the severity of the curvature within the spine.

Minor curves require external bracing during the growing period in a child's life, but if the curve becomes more severe either in childhood or in adult life, major surgical straightening and correction is required to prevent otherwise severe progressive deformities of the spine, chest wall, and other organs within the chest and abdomen.

For a period of approximately 25 years the major method of treating severe spine curvatures surgically is the use of an implantable stainless steel rod which is placed adjacent to vertebral bodies and is hooked into the vertebral bodies in the portions on the posterior aspect called "laminae". Two hooks are placed at either end of the rod and the proximal or upper portion of the rod is ratcheted over a 2 inch portion of the length of the rod. This allows the hook with a small shoulder or ridge on the inside of the surface to fit onto the rod. This construction allows the hook to be moved along the rod in a series of steps thus distracting the two ends of the curvature through the vertebral bodies. Downward movement of the hook is prevented along the rods since the ridge on the interior portion of the opening of the hook interacts with the ratchet on the rod and the hook is displaced from its perpendicular orientation to the axis of the rod. If the hook is normal to the longitudinal axis of the rod it slides easily over the ratchet. However, if it is displaced from there, the ridge will be retained on the surface of each ratchet by preventing movement. Distraction forces are then applied to the vertebrae to correct and stabilize their orientation based on the ratchet principle on the concave side of the spine. This system is utilized not only for scoliosis but also to stabilize an otherwise fractured spine where two rods are used on either side of the spine and usually one or two vertebral bodies above the fractured level.

Although the Harrington rod system provides a very effective means of straightening the curved spine it unfortunately cannot solely maintain this position.

If a patient were to stand up shortly after surgery the weakest portion of the system is bone at the upper end of the rod termed the lamina, usually in the thoracic area. In this case when the patient became erect and the spine was loaded, the top hook would pull out of the bone taking a portion of the lamina with it and the system would then collapse and fail.

Because the spine in scoliosis is curved in a very complex, three dimensional manner, it is not possible to spread the load out in a routine fashion over more than one lamina as it is impossible to put on more than one hook on the ratchet system on a straight rod where the depth and rotation of each individual vertebra vary so considerably and also varies during the entire straightening process and thus only one hook can be used to take all the load in the proximal portion of the spine.

Once this straightening is obtained, in order to maintain the correction, bone fusion chips are taken from the hip area and the entire spine between the two hooks at either end of the correcting system is then covered with bone chips and bone graft which will eventually grow to incorporate the rods and the fusion mass into the entire area of the spine which has been straightened, corrected and fused.

A period of several months however is required until the fusion process is complete. During this time the spine must not be unduly loaded and thus external protection is required.

In the initial post-operative phase of anywhere from two to four weeks, the patient is kept recumbent on a special rigid frame termed the stryker bed.

At the end of this time, the patient is then placed in a full body cast and is allowed to be up walking. This cast prevents flexion, extension and rotatary forces being applied to the upper distraction hook at its insertion site. It takes anywhere from six to nine months before the fusion is solid and during this period of time the external supporting body cast is worn. The greatest disadvantage of the Harrington system is that all the load has been taken on one vertebral level at the upper end which is the weakest point of the system and more hooks could not be applied because the hooks lacked the ability to adjust and compensate for the different and constantly changing spine during the corrective procedure. If this were feasible the load could be distributed over a much greater area of the spine and yet allow fusion to occur while the patient could be up walking without external support.

SUMMARY OF THE INVENTION

Accordingly, it is an object of the present invention to at least partially overcome these disadvantages by providing an adjustable hook wherein the distance between the rod which is inserted through an opening in one end of the hook and the selected vertebra which is attached to the other end of the hook, is adjustable.

To this end, in one of its aspects, the invention provides a hook for use with a rod for the treatment of spinal disorders, said hook comprising:

a body portion having a housing portion at one end, a hooked portion at the other end, said housing portion having a channel therethrough;

a sleeve adapted to be inserted and retained in said channel; and retaining means to retain said sleeve in said channel.

In another of its aspects, the invention further provides a hook for use with a Harrington rod for the treatment of spinal disorders, said hook comprising:

a stainless steel body portion having a housing portion with a flat, upper surface, at one end, and a substantially U-shaped hook at the other end, the height of the hook being greater than the height of said housing portion, said housing portion having an elliptically-shaped channel therethrough;

a cylindrical, stainless steel sleeve adapted to be inserted and retained in said channel, said sleeve having a first retaining lip on one surface and a second retaining lip on the opposite surface, said first retaining lip being truncated along two opposite sides, the outer diameter of the second retaining lip being greater than the width of said channel, and the outer diameter of said first retaining lip across said truncated sides being less than the width of said channel, the length of said sleeve being greater than the length of said channel;

a ridge on the interior surface of said sleeve at approximately one-half the length of said sleeve;

a stainless steel, resilient C-shaped locking ring adapted to be inserted on said sleeve between said first retaining lip and the top of said housing portion when said sleeve is inserted through said channel.

Further objects and advantages of the invention will appear from the following description taken together with the accompanying drawings.

BRIEF DESCRIPTION OF THE DRAWINGS

FIG. 1 is a perspective view of a rod for use with the present invention.

FIG. 2 is a side view of the assembled hook of the present invention.

FIG. 3 is a top view of the body portion of the hook of FIG. 2.

FIG. 4 is a section view along line IV—IV of FIG. 3.

FIG. 5 is a top view of the sleeve of the hood of FIG. 2.

FIG. 6 is a side view of the sleeve of FIG. 5.

FIG. 7 is a top view of the retaining means of the hook of FIG. 2.

DESCRIPTION OF THE PREFERRED EMBODIMENT

Referring first to FIG. 1, there is shown a perspective view of a rod for use with the present invention. This rod is the same rod presently being used in the Harrington System and is well known in the prior art. It is commonly referred to in the industry as the Harrington Rod, and is commercially available from several companies, including Zimmer USA of Warsaw, Indiana, U.S.A.

The rod 10 is generally made of stainless steel although it could be manufactured of any material suitable for implanting in a living body. The rod 10 is generally a cylindrical rod and may be made of any desired length. It comprises an upper portion 12, a lower portion 14 and a collar 16.

The upper portion 12 of rod 10 comprises a plurality of coaxial notches 18 and a short, plain cylindrical protruding end 20. The lower portion 14 of rod 10 comprises a plain, cylindrical casing 15 and a short, protruding end 22. A collar 16 is affixed to the end of the casing 15 adjacent the protruding end 22. As stated before, the length of rod 10 may vary as well as the lengths of the upper portion 12 and the lower portion 14.

Referring now to FIG. 2, there is shown a side view of the assembled hook of the present invention. The hook 24 comprises a body portion 26, a sleeve 28 and a retaining means 30. The structure of each of these components and their respective uses will now be explained with reference to the remaining figures and the following description.

FIG. 3 is a top view of the body portion 26 of the hook 24. The body portion 26 is comprised of a housing portion 36 and a hooked portion 34. The housing portion 36 has a substantially flat top surface 33 with a channel 32 through the central part thereof. The channel 32 is substantially oblong or elliptical in shape and the hooked portion 34 is substantially U-shaped.

FIG. 4 is a sectional view along line IV—IV of FIG. 3. Channel 32 is shown extending the height of housing portion 36. Hooked portion 34 is a substantially U-shaped hooked portion and its height is marginally greater than the height of the housing portion 36.

FIG. 5 shows a top view and FIG. 6 shows a side view of the sleeve 28. The sleeve 28 has a cylindrical middle portion 40 with a circular hole 46 (top view) therethrough. A first retaining lip 42 is at one end of the middle portion 40 and a second retaining lip 44 is at the opposite end thereof.

The lips 42 and 44 are identical except that two sides of the first retaining lip 42 are truncated as shown in FIG. 5. The outer diameter of the lips 42, 44 is greater than the diameter of the hole 46 and is larger than the width of the channel 32. However, the distance across the truncated sides of the retaining lip 42 is marginally less than the width of the channel 32, thus allowing the sleeve to be inserted through the channel 32 by inserting lip 42 therethrough until the lip 44 comes into contact with the bottom surface of the housing portion 36.

The inside surface of sleeve 28 carries a small shoulder 49. This shoulder 49 is used to interact with the notches 18 as is well known in the prior art.

FIG. 7 shows a retaining means 30 which in the preferred embodiment, is a C-shaped ring, which is used to secure the sleeve 28 to the body portion 26 as will be explained hereinafter.

In order to assemble the device, the sleeve 28 is first inserted through the channel 32 by inserting lip 42 first through the bottom opening of the channel 32. The sleeve 28 is then pushed through the channel 32 until the lip 44 comes into contact with the undersurface of the housing portion 36. The retaining means 30 is then inserted on the sleeve 28 between the lip 42 and the top surface of the housing portion 36. The height of the middle portion 40 of sleeve 28 is greater than the height of the opening 32 thus allowing the retaining means 30 to be inserted on the sleeve 28. The curvature of the inside surface of the retaining means 30 is such that it fits around the outside surface of the sleeve 28. The retaining means 30 has a certain amount of resiliency to it to allow it to be opened slightly and forced around the sleeve. Once it is inserted on sleeve 28, it springs back to its original position thereby securing the sleeve 28 in the opening 32.

When the device is assembled, the sleeve 28 has lateral movement in the opening 32 and can also be rotatable therein. Thus, the distance between the center axis of the circular opening in the sleeve and the hooked portion 34 may be varied, with the parameters of the length of the opening 32.

The use of this device, in conjunction with rod 10, provides distinct advantages over the prior art devices as will now be explained. This device allows a plurality of hooks to be used in the medical procedure to correct spinal disorders. The main advantage is that it distributes the tension over several vertebrae in the spine and thus, has remarkably simplified the procedure and has effectively eliminated the need for long immobilization following corrective surgery.

In the procedure using the present device, rod 10 is first implanted adjacent the spinal column as is done in the prior art. The assembled hook is placed over the rod and the hook is attached to a selected vertebrae. As with the prior art, the hook is ratcheded upwardly until the vertebrae which is at the greatest distance from the rod is secured. Since the spine is curved, the distance between the vertebrae and the rod will vary, depending upon the point in the curvature of the vertebrae. Distraction then takes place in the operating room over several hours and the hook is moved upwardly as far as possible, until the spine is as straight as possible. The procedure is then repeated from the tip of the rod and from the bottom of the rod until a number of hooks are secured in place.

Since the distance between the center axis of the sleeve 28 and the hooked portion 34 is variable as the sleeve 28 has lateral movement in the opening 32, it is possible to secure vertebrae to the rod which are at different points on the curvature of the spine. It is therefore possible to secure more than two hooks to selected vertebrae at the same time and the tension will be distributed over all the hooks secured.

With the use of the present invention, it is possible in many cases to significantly reduce the time of immobilization of the patient. Spinal fusion may still be indicated although with the present procedure, the time required for immobilization is shortened and the immobilization procedure may in itself be simplified. In most cases, the need for complicated braces and body casts has been eliminated. This is a tremendous advantage and much improves the patient's welfare.

Various modifications of the device may be made within the spirit and scope of the present invention. The component parts may be manufactured of any suitable material for implanting in the body and preferably, are made of stainless steel.

Further, the shape and configuration of the hook may also vary, as is well known. A sharp edge on the hook facilitates engagement at the purchase site with minimal trauma whereas a blunt hook is preferred after the purchase site and direction of the hook are established. A blunt hook is also preferred in an inferior purchase site. The hook may be rubbed with a triangular rib which prevents lateral rotation and drift. Further, if desired, a C washer may be used to lock the superior hook engaged in the ratchet portion of the distraction rod into the final position. This washer could be replaced, if desired, with a hex nut which serves the same purpose.

Although the disclosure describes and illustrates a preferred embodiment of the invention, it is to be understood the invention is not restricted to this particular embodiment.

What I claim is:

1. A hook for use with a rod for the treatment of spinal disorders, said hook comprising:
   a body portion having a housing portion at one end, a hooked portion at the other end, said housing portion having a channel therethrough;
   a sleeve adapted to be inserted and retained in said channel; and
   retaining means to retain said sleeve in said channel, said retaining means comprising a C-shaped locking ring inserted on said sleeve to retain said sleeve in said channel.

2. A hook as claimed in claim 1 wherein said channel is elliptical in shape.

3. A hook as claimed in claim 2 wherein said sleeve is cylindrical in shape.

4. A hook as claimed in claim 3 wherein said sleeve has a first retaining lip on one surface and a second retaining lip on the opposite surface.

5. A hook as claimed in claim 4 wherein said first retaining lip is truncated along two opposite sides thereof.

6. A hook as claimed in claim 5 wherein the outer diameter of the second retaining lip is greater than the width of said channel, and the outer diameter of said first retaining lip across said truncated sides is less than the width of said channel.

7. A hook as claimed in claim 6 wherein the length of said sleeve is greater than the length of said channel, and said C-shaped locking ring is inserted on said sleeve between said first retaining lip and the top of said housing portion when said sleeve is inserted through said channel.

8. A hook as claimed in claim 8 wherein the interior surface of said sleeve has a ridge thereon.

9. A hook as claimed in claim 8 wherein said ridge is at approximately one-half the length of said sleeve.

10. A hook as claimed in claim 1 wherein said body portion, said sleeve and said retaining means are made of stainless steel.

11. A hook as claimed in claim 2 wherein said housing portion has a substantially flat upper surface.

12. A hook as claimed in claim 1 wherein said hooked portion is a substantially U-shaped hook.

13. A hook as claimed in claim 12 wherein the height of said hook is marginally greater than the height of said housing portion.

14. A hook for use with a Harrington rod for the treatment of spinal disorders, said hook comprising:
   a stainless steel body portion having a housing portion with a flat, upper surface, at one end, and a substantially U-shaped hook at the other end, the height of the hook being greater than the height of said housing portion, said housing portion having an elliptically-shaped channel therethrough;
   a cylindrical, stainless steel sleeve adapted to be inserted and retained in said channel, said sleeve having a first retaining lip on one surface and a second retaining lip on the opposite surface, said first retaining lip being truncated along two opposite sides, the outer diameter of the second retaining lip being greater than the width of said channel, and the outer diameter of said first retaining lip across said truncated sides being less than the width of said channel, the length of said sleeve being greater than the length of said channel;
   a ridge on the interior surface of said sleeve at approximately one-half the length of said sleeve;
   a stainless steel, resilient C-shaped locking ring adapted to be inserted on said sleeve between said first retaining lip and the top of said housing portion when said sleeve is inserted through said channel.

* * * * *